United States Patent [19]

Walkow et al.

[11] 4,400,458

[45] Aug. 23, 1983

[54] DIAZONIUM SALTS AND A DIAZO-TYPE MATERIAL COMPRISING THESE DIAZONIUM SALTS

[75] Inventors: Fred Walkow, Wolfen; Peter Czerney, Weimar; Horst Hartmann, Dresden; Jörg Marx, Dessau, all of German Democratic Rep.

[73] Assignee: VEB Filmfabrik Wolfen, Wolfen, German Democratic Rep.

[21] Appl. No.: 302,286

[22] Filed: Sep. 14, 1981

[30] Foreign Application Priority Data

Dec. 15, 1980 [DD] German Democratic Rep. ... 226068

[51] Int. Cl.³ .................. G03C 1/54; C07C 113/04
[52] U.S. Cl. ..................... 430/157; 260/141;
430/141; 430/146; 430/150; 430/163; 430/171;
430/173; 430/176; 430/177; 430/180; 430/182;
430/183; 430/186
[58] Field of Search .................. 260/141 H, 141 R;
430/141, 146, 157, 171, 183, 186, 163, 176, 180,
177, 182, 173, 150

[56] References Cited

U.S. PATENT DOCUMENTS

| | | | |
|---|---|---|---|
| T903,022 | 10/1972 | Borden | 430/183 |
| 2,378,583 | 6/1945 | Schmidt | 430/157 |
| 3,288,804 | 11/1966 | Fleck et al. | 260/141 H |
| 3,401,038 | 9/1968 | Panasik et al. | 430/171 |
| 3,486,900 | 12/1969 | Tsunoda et al. | 430/171 |
| 3,663,560 | 5/1972 | Schellhammer et al. | 260/141 H |
| 3,743,509 | 7/1973 | Baltazzi et al. | 430/183 |
| 4,147,552 | 4/1959 | Specht et al. | 430/152 |

FOREIGN PATENT DOCUMENTS 1250252 10/1971 United Kingdom ............... 430/171

OTHER PUBLICATIONS

Dinaburg, "Photosensitive Diazo Cpds", Focal Press, 1964, pp. 22–25.
Landau, R. et al., *J. of Photo Science*, vol. 13, 1965, pp. 144–151.

*Primary Examiner*—Charles L. Bowers, Jr.
*Attorney, Agent, or Firm*—Jordan and Hamburg

[57] ABSTRACT

It is the purpose and object of the present invention to make better use of the emission range of light sources and to create the diazonium salts necessary for such purpose. The diazonium salts of the present invention of the general formula

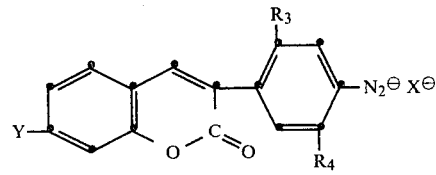

wherein
Y is

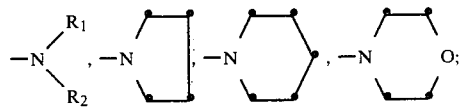

$R_1$, $R_2$ are equal or different and are, alkyl having 1 to 10 carbon atoms, aryl having 6 to 10 carbon atoms in a mono or polycylic ring;
$R_3$ is hydrogen, halogen, alkyl, alkoxy, cyano;
$R_4$ is hydrogen, halogen, alkyl, alkoxy; and
$X^e$ is an anion, can be employed with all known couplers and additives in diazotype materials. They have an absorption range of 480 to 550 nm.

22 Claims, No Drawings

DIAZONIUM SALTS AND A DIAZO-TYPE MATERIAL COMPRISING THESE DIAZONIUM SALTS

BACKGROUND OF THE INVENTION AND PRIOR ART STATEMENT

This invention relates to diazonium salts and a diazo-type material containing these salts for information-recording by means of light.

The operating principle of diazo printing involves producing a positive image on layers of solid binding agents provided on a polymer base by decomposing a diazonium salt through the action of light and, subsequently, reacting the unconnected diazonium salt with a coupler also provided in the layer of binding agents through the action of alkali agents, forming an azo dyestuff.

Previously, 4-dialkylaminobenzene-diazonium salts have been preferably used as light-sensitive diazonium compounds which may, in addition, comprise additional substances. Such compounds have absorption maxima between 380–410 nm (DE-OS Nos. 2 024 243, 1 693 195). It is possible to obtain an absorption maximum of 471 nm in the case of 5-methoxy-4-morpholino-2-nitrobenzenediazonium tetra fluoroborate (DE-OS No. 1 202 251). A more extensive bathochromy cannot be achieved with benzene diazonium salts.

The utilization of this kind of diazonium salt requires the use of energy-intensive, high-pressure mercury-vapor lamps, while the light emitted by them can only be partly utilized.

Light sources which radiate light in longer wave lengths, such as tungsten or halogen lamps, are not appropriate for the illumination of diazo-type materials that contain benzene diazonium salts.

Diazonium salts with absorption maxima around 560 nm have also been proposed (DD-WP G 03 c/213 282), which are sensitive to wave lengths from 540 to 600 nm. Even when these substances are used, only part of the lamp emissions can be used in photolysis.

It is the purpose of this invention to take advantage of the longer wave range of the lamp emissions and to expand the absorption range of the present diazonium salts.

SUMMARY OF THE INVENTION

The known diazonium salts have absorption maxima in the range of 380 to 480 or 540 to 600 nm. However, a possibly wide absorption of the light-sensitive components is desirable. It is thus the object of the present invention to locate diazonium salts which are sensitive to light ranges in wave lengths from 480 to 550 nm in order to produce diazo-type materials with such compounds. This goal is accomplished in accordance with this invention in that the light-sensitive diazonium salt constitutes a compound of the general formula

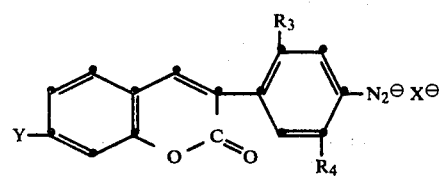

wherein
Y is

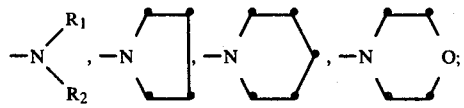

$R_1$, $R_2$ may be equal or different, and are alkyl having 1 to 10 carbon atoms, aryl having 6 to 10 carbon atoms in a mono or polycyclic ring;
$R_3$ is hydrogen, halogen, alkyl, alkoxy, cyano;
$R_4$ is hydrogen, halogen, alkyl, alkoxy; and
$x^\ominus$ is an anion, and the diazo-type material in the light-sensitive layer is a diazonium salt of the general formula

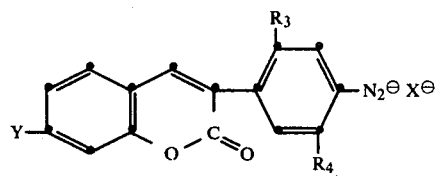

wherein
Y is

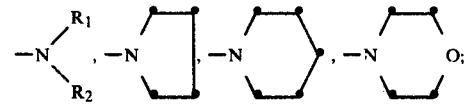

$R_1$, $R_2$ may be equal or different and are alkyl having 1 to 10 carbon atoms, aryl having 6 to 10 carbon atoms in a mono or polycyclic ring;
$R_3$ is hydrogen, halogen, alkyl, alkoxy, cyano;
$R_4$ is hydrogen, halogen, alkyl, alkoxy; and
$x^\ominus$ is an anion.

DETAILED DESCRIPTION OF PREFERRED EMBODIMENTS

All substances usually so employed in diazo printing, such as tetrafluoroborate, p-chlorobenzene sulfonate, sulfate, phosphate, nitrate, chloride, zinc chloride, stannic chloride, manganese chloride or cadmium chloride may be used as the anion for the diazonium salts of the present invention.

In the manufacture of diazo-type recording materials, the diazonium compounds of the present invention may be combined with the usual couplers. Some advantageous couplers are the 2-hydroxy-3-naphthanilides, the 2,3-dihydroxynaphthalenes and cyano-acetic acidamides. To produce diazo-type casting solutions, diazonium salts and couplers are initially mixed, wherein the coupler should be at least 0.1 mole in excess, and then dispersed in a polymer solution. Here, about 20 to 40 parts by weight of the mixture should correspond to 100 parts by weight of binding agent.

Cellulose derivatives, vinyl polymers, copolymers of vinyl chloride and vinyl acetate, polystyrenes, copolymers of alkylacrylates and acrylic acid, and polyethylene oxides are especially suitable polymeric binding agents.

The material may further comprise the usual additives, such as UV-absorbers, stabilizers, light-protective substances, developing accelerators and plasticizers.

The diazo-type materials may be manufactured by affixing a casting solution onto a carrier layer of a transparent polymer or paper sheet. This may be illuminated in the usual way and developed into positive azo-dyestuff images. Mercury arc lamps, carbon arc lamps, nitrophoto lamps and also halogen or tungsten lamps, may be employed as light sources, which creates a wide field of application.

EXAMPLES OF EMBODIMENTS

(a) Example 1

4-n,n-dimethylaminosalicylaldehyde is condensed with 4-nitrobenzenecyanide in an alcoholic solution under the action of piperidine, wherein 3-[4'-nitrophenyl]-7-dimethylaminoiminocoumarin is also formed at the same time with splitting off of water. After separation from the reactive solution, the compound is saponified in ethanol into the corresponding coumarin with the aid of hydrochloric acid, which separates as a red-orange dyestuff. The nitro group is reduced with zinc powder in glacial acetic acid. The strongly fluorescent amine obtained is subsequently diazotized in a hydrochloric acid solution with sodium nitrite. The coumarin is then precipitated as 3-[4'-diazoniumphenyl]-7-dimethylamino-coumarin-tetrafluoroborate with the aid of sodium tetrafluoroborate. The absorption maximum lies at 505 nm.

EXAMPLE 2

4-n,n-phenyl-aminosalicylaldehyde is condensed with 2,5-dimethoxy-4-nitrobenzene-cyanide in an alcoholic solution under the influence of piperidine, wherein dimethoxy-[4'-nitrophenyl]-7 phenylethylaminiminocoumarin is formed with splitting-off of water. After separation from the reactive solution, this compound is saponified in ethanol with the aid of hydrochloric acid into the corresponding coumarin, which precipitates. The nitro group is reduced with zinc powder in glacial acetic acid. The strongly fluorescent amine obtained is subsequently diazotized in a hydrochloric acid solution with sodium nitrate. The 3-(4'-diazoniumphenyl-2',5'-dimethoxy)-7-phenylethylaminocoumarin tetrafluoroborate (absorption maximum 510 nm) is then precipitated with the aid of sodium tetrafluoroborate.

3-[4'-diazoniumphenyl]-7-di-n-butylaminocoumarin-tetrachlorozincate (507 nm),

3-[4'-diazoniumphenyl]-7-diethylaminocoumarin-tetrafluoroborate (508 nm), and

3-[4'-diazoniumphenyl]-7-pyrrolidinocoumarin-tetrachlorozincate (503 nm) were further produced in the above described manner.

(b) Application

EXAMPLE 3

10 g 3-[4'-diazoniumphenyl]-7-dimethylaminocoumarin tetrafluoroborate 10 g 2,3-dihydroxynaphthaline, and 2 g sulfosalicyclic acid are dispersed in a 1000 ml 7.5% cellulose acetate solution in $CH_2Cl_2/CH_3OH$ and poured onto a polymeric base. After illumination with a mercury high-pressure radiator and development by ammonia vapor, a red-brown image is formed.

EXAMPLE 4

12 g 3-[4-diazoniumphenyl]-7-dibutylaminocoumarin-tetrachlorozincate and 7 g β-naphthol are dissolved in 1000 ml of a 7.5% cellulose acetate solution in $CH_2Cl/CH_3OH$ and poured as a film onto a polymeric carrier material. Illumination through a line grating with a xenon high-pressure radiator and subsequent development by ammonia vapor result in a positive red dyestuff image.

EXAMPLE 5

11 g 3-[4'-diazoniumphenyl]-7-pyrrolidinocoumarin tetrachlorozincate 7 g acetoacetanilide and 2 g sulfosalicylic acid are dissolved in a 100 ml 7.5% cellulose acetate solution in $CH_2Cl_2/CH_3OH$ and poured as a film onto a polymeric carrier material. Illumination through a line grating with a 500 W tungsten lamp and subsequent development by ammonia result in a positive yellow dyestuff image.

EXAMPLE 6

11 g 3-[4'-diazoniumphenyl]-diethylaminocoumarin tetrafluoroborate, 3 g 2-hydroxy-3-naphthalenic acid-[2'-methoxy-anilide], 20 g β-napthol, 2 g acetoacetanilide, and 2 g sulfosalicyclic acid are dissolved in a 1000 ml 4.5% cellulose acetate solution in $CH_2Cl_2/CH_3OH$ and poured as a film onto a polymeric carrier material. Illumination through a line grating with a halogen lamp and subsequent development by ammonia vapor results in a positive brown dyestuff image.

EXAMPLE 7

11 g 3[4'-diazoniumphenyl]-7-diethylaminocoumarin tetrachlorozincate, and 2 g sulfosalicyclic acid are dissolved in 1000 ml 7.5% cellulose acetate solution in $CH_2Cl_2/CH_3OH$ and poured as a film onto a polymeric carrier material. Illumination through a line grating with a halogen lamp and development by the moisture process at a constant $\geq 8$ pH with a phloroglucine and 2-hydroxy-3-naphthoic acid-ethylamide results in a positive reddish-brown dyestuff image,

We claim:

1. A light-sensitive diazonium salt of the general formula

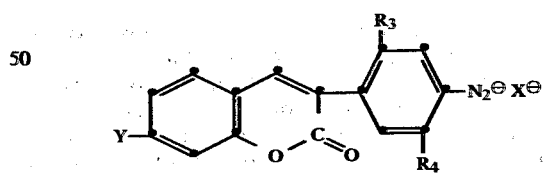

wherein
Y is

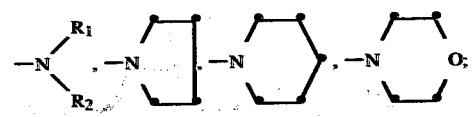

$R_1$, $R_2$ are equal or different, and are alkyl having 1 to 10 carbon atoms, aryl having 6 to 10 carbon atoms in a mono or polycyclic ring;

$R_3$ is hydrogen, halogen, alkyl, alkoxy, cyano;

$R_4$ is hydrogen, halogen, alkyl, alkoxy; and $X^\ominus$ is an anion.

2. A diazo-type material, comprising a diazonium salt in the light-sensitive layer of the general formula

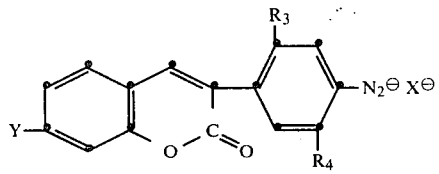

wherein
Y is

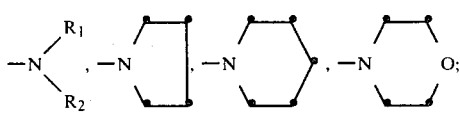

$R_1$, $R_2$ are equal or different, and are alkyl having 1 to 10 carbon atoms, aryl having 6 to 10 carbon atoms in a mono or polycyclic ring;

$R_3$ is hydrogen, halogen, alkyl, alkoxy, cyano;

$R_4$ is hydrogen, halogen, alkyl, alkoxy; and $X^\ominus$ is an anion.

3. The compound of claim 1 which is 3-(4'-diazoniumphenyl)-7-dimethylamino coumarin.

4. The compound of claim 1 which is 3-(4'-diazoniumphenyl-2',5'-dimethoxy)-7-phenylethylamino coumarin.

5. The compound of claim 1 which is 3-(4'-diazoniumphenyl)-7-di-n-butylamino coumarin.

6. The compound of claim 1 which is 3-(4'-diazoniumphenyl)-7-diethylamino coumarin.

7. The compound of claim 1 which is 3-(4'-diazoniumphenyl)-7-pyrrolidino coumarin.

8. The compound of claim 1 wherein said anion X is selected from the group consisting of tetrafluoroborate, p-chlorobenzene sulfonate, sulfate, phosphate, nitrate, chloride, zinc chloride, stannic chloride, manganese chloride, cadmium chloride.

9. The material of claim 2 wherein said diazonium salt is sensitive to light at a wavelength from 480 to 550 nm.

10. The material of claim 9 additionally comprising a coupler.

11. The material of claim 10 wherein said coupler is selected from the group consisting of 2-hydroxy-3-naphthanilides, 2,3-dihydroxynaphthalines, cyanoacetic acidamides, and mixtures thereof.

12. The material of claim 10 additionally comprising a polymeric bonding agent.

13. The material of claim 12 wherein said polymeric binding agent is selected from the group consisting of cellulose derivatives, vinyl polymers, copolymers of vinyl chloride and vinyl acetate, polystyrene, copolymers or alkylacrylates and acrylic acid, polyethylene oxides.

14. The material of claim 12 additionally comprising a component selected from the group consisting of UV-absorbers, stabilizing agents, light protective substances, developing accelerators, plasticizers.

15. The material of claim 9 wherein said anion X is selected from the group consisting of tetrafluoroborate, p-chlorobenzene, sulfonate, sulfate, phosphate, nitrate, chloride, zinc chloride, stannic chloride, manganese chloride, cadmium chloride.

16. The material of claim 15 wherein 3-(4'-diazoniumphenyl)-7-dimethylamino coumarin tetrafluoroborate, dihydroxynaphthalene, and sulfosalicyclic acid are all dispersed in a cellulose acetate solution and then deposited on a polymeric base.

17. The material of claim 15 wherein 3-(4-diazoniumphenyl)-7-dibutylamino coumarin tetrachlorozincate, and β-naphthol are dissolved in a cellulose acetate solution and deposited on a polymeric carrier.

18. The material of claim 15 wherein 3-(4'-diazoniumphenyl)-7-pyrrolidino coumarin tetrachlorozincate, acetoacetanilide, and sulfosalicyclic acid are all dissolved in a cellulose acetate solution and deposited on a polymeric carrier.

19. The material of claim 15 wherein 3-(4'-diazoniumphenyl)-diethylamino coumarin tetrafluoroborate, 2-hydroxy-3-naphthalenic acid-(2'-methoxy anilide), β-naphthol, acetoacetanilide, and sulfosalicyclic acid are all dissolved in a cellulose acetate solution and deposited onto a polymeric carrier material.

20. The material of claim 15 wherein 3-(4'-diazoniumphenyl)-7-diethylamino coumarin tetrachlorozincate and sulfosalicyclic acid are dissolved in a cellulose acetate solution and deposited onto a polymeric carrier.

21. The material of claim 12 wherein said coupler is present in at least about a 0.1 mole excess over said diazonium salt.

22. The material of claim 21 wherein about 20 to 40 parts by weight of said diazonium salt and coupler are present to about 100 parts by weight of said polymeric binding agent.

* * * * *